United States Patent [19]

Küster et al.

[11] 4,237,067

[45] Dec. 2, 1980

[54] PROCESS FOR THE MANUFACTURE OF α,β-UNSATURATED N-SUBSTITUTED CARBOXYLIC ACID AMIDES

[75] Inventors: Erich Küster, Krefeld; Bernhard Goossens, Velbert; Eduard Barthell, Krefeld; Kurt Dahmen, Monchen-Gladbach, all of Fed. Rep. of Germany

[73] Assignee: Chemische Fabrik Stockhausen & Cie., Krefeld, Fed. Rep. of Germany

[21] Appl. No.: 35,756

[22] Filed: May 3, 1979

[30] Foreign Application Priority Data

May 5, 1978 [DE] Fed. Rep. of Germany ....... 2819735
Aug. 21, 1978 [DE] Fed. Rep. of Germany ....... 2836520

[51] Int. Cl.$^3$ ............................................ C07C 102/00
[52] U.S. Cl. ....................................... 564/205; 564/206
[58] Field of Search ...................... 260/561 N, 561 B

[56] References Cited

U.S. PATENT DOCUMENTS

| | | | |
|---|---|---|---|
| 2,354,585 | 12/1950 | Erickson | 260/561 N |
| 3,914,303 | 10/1975 | Danihet et al. | 260/561 N |

FOREIGN PATENT DOCUMENTS

737195  6/1952  United Kingdom ................ 260/561 N

OTHER PUBLICATIONS

Galat et al., J. Am. Chem. Soc. 65 (1943), pp. 1566–1567.
Buhler et al., Survey of Organic Syntheses; John Wiley & Sons, N.Y., N.Y., vol. 2, 1978, pp. 825–826.
Wagner et al. Synthetic Organic Chemistry, John Wiley & Sons, N.Y., N.Y., 1955, p. 568.
Sano et al., Chem. Abst., 80 (1974), #120351 and 120352.

*Primary Examiner*—Arthur P. Demers
*Attorney, Agent, or Firm*—Sprung, Felfe, Horn, Lynch & Kramer

[57] ABSTRACT

Process for the manufacture of α,β-unsaturated N-substituted carboxylic acid amides of the general formula $$\begin{array}{c}H\\ \diagdown \\ R^1\end{array}C=C\begin{array}{c}R^2\\ \diagup \\ \diagdown \\ C-NH-(Y)-R^3\\ \parallel \\ O\end{array} \quad (I)$$

in which
$R^1$ represents H or $CH_3$
$R^2$ represents H or $CH_3$, and
Y represents a divalent straight-chain or branched organic radical having 2–30 carbon atoms, and
$R^3$ represents H or the radical of an amine of the formula $-N(R^4)(R^5)$, in which $R^4$ and $R^5$ represent alkyl radicals having 1 to 4 carbon atoms, by reacting β-substituted carboxylic acid amides of the formula $$\begin{array}{c} R^1\ H\\ |\ \ |\\ Z-C-C-C\\ |\ \ |\ \ \diagdown\\ H\ R^2\ \ NH_2\end{array}\begin{array}{c}O\\ \diagup\\ \end{array} \quad (II)$$

in which
Z represents OH or the radical $R^6O-$, in which $R^6$ is an alkyl radical having 1 to 4 carbon atoms,
with amines of the general formula $$H_2N-(Y)-R_3 \qquad III$$

at temperatures in the range of 100° to 200° C., preferably 120° to 175° C., with the elimination of ammonia, and heating the resulting N-substituted β-hydroxycarboxylic or β-alkoxycarboxylic acid amides in the presence of catalysts, water or alcohol, respectively, being split off. The water is split off at temperatures of 100°–250° C. with acidic catalysts such as phosphoric acid, or basic catalysts such as sodium hydroxide, and alcohol is split off at 70°–150° C. with basic catalysts such as sodium or potassium hydroxide. The reaction product is separated by distillation, optionally in vacuo.

11 Claims, No Drawings

PROCESS FOR THE MANUFACTURE OF α,β-UNSATURATED N-SUBSTITUTED CARBOXYLIC ACID AMIDES

The invention relates to a process for the manufacture of α,β-unsaturated N-substituted carboxylic acid amides.

N-substituted alkylacrylamides have been known for a long time. They can be produced by reacting acrylonitrile with 1-olefins (JACS 73, (1951),, 4076), and by reacting primary or secondary amines with an addition compound of maleic acid anhydride and triphenyl phosphine (JP-PS 6920083). According to GB-PS 746747, N-substituted acrylamides may be obtained by the dehydrohalogenation of β-chloropropionic acid amides, and according to DE-OS 2344070 by the pyrolysis of β-methoxypropionic acid amides. They may furthermore be produced according to the Schotten-Baumann reaction process, by reacting acrylic chloride with corresponding diamines (US-PS No. 2951907), by the catalytic addition of functionalized amines to acetylene in a CO - atmosphere (UP-PS No. 2773063), by the reductive amination of diacetone acrylamide (J. Polym. Sci. 10 (1972), 595), and by the pyrolysis of norbornene derivatives (DE-OS No. 2354602). Finally, these compounds are also obtained according to the processes described in DE-OS No. 2502247, DE-OS No. 2656682 and US-PS No. 3878247 by adding amines to acrylates or methacrylates with simultaneous aminolysis, resulting in N-substituted β-aminopropionic acid amides which are split by pyrolysis to form the corresponding α,β-unsaturated N-substituted carboxylic acid amides.

All of the known processes use expensive and highly toxic starting materials, require high expenditure and usually produce only modest yields. A technically simple process which produces high yields of α,β-unsaturated N-substituted carboxylic acid amides would therefore be desirable.

The subject of the invention is a process for the manufacture of α,β-unsaturated N-substituted acid amides of the general formula

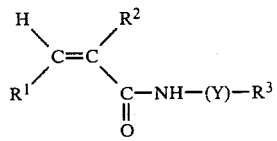  (I)

in which
 $R^1$ represents H or $CH_3$
 $R^2$ represents H or $CH_3$, and
 Y represents a straight-chain or branched divalent organic radical having 2–30, preferably 2–18, carbon atoms, preferably a group of the formula $-(Y_1)_m-(Y_2)_n-(Y_3)_t$, in which $Y_1$, $Y_2$ and $Y_3$ represent an alkylene group or the radical of a cyclic organic ring system having 5 or 6 carbon atoms, and the sum of m, n and t is 2 or 3, and
 $R^3$ represents H or the radical of an amine of the formula $-N(R^4)(R^5)$, in which $R^4$ and $R^5$ represent alkyl radicals having 1 to 4 carbon atoms,
characterized in that β-substituted carboxylic acid amides of the general formula

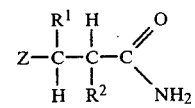  (II)

in which
 $R^1$ and $R^2$ have the meaning given above, and
 Z represents a hydroxy group or an alkoxy radical of the formula $R^6O-$, in which $R^6$ is an alkyl radical having 1 to 4 carbon atoms,
are transamidated with amines of the general formula

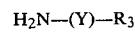  (III)

in which Y and $R_3$ have the meaning given above, at temperatures of about 100° to 200° C., preferably about 120° to 175° C., with the elimination of ammonia, and the resulting N— substituted β-hydroxycarboxylic or β-alkoxycarboxylic acid amides are converted by heating, in the presence of catalysts, into the N-substituted α,β-unsaturated carboxylic acid amides and these are isolated.

The divalent organic radical Y in formulae (I) and (III) may be a straight-chain or branched alkylene radical that is optionally substituted. Examples of substituents are aryl radicals such as the substituted or unsubstituted phenyl radical. When Y represents a group of the formula—$(Y_1)_m-(Y_2)_n-(Y_3)_t$, each of the radicals $Y_1$, $Y_2$ and $Y_3$ may represent a straight-chain or branched optionally substituted alkylene group or the radical of a cyclic organic ring system having 5 or 6 carbon atoms. The cycloalkyl radical may optionally likewise be substituted, for example by alkyl.

When $R_3$ represents the radical of an amine of the formula—$N(R^4)(R^5)$, the radicals $R^4$ and $R^5$, which may be the same or different, may be straight-chain or branched alkyl radicals, for example, methyl, ethyl, propyl, isopropyl or n-butyl radicals.

In the same manner Z in the formula (II) represents an OH-group or an alkoxy radical of the formula $R^6O-$, in which $R^6$ represents an alkyl radical having 1 to 4 carbon atoms, such as, for example, the methyl, ethyl, propyl, isopropyl or n-butyl radical.

The smooth course of the transamidation reaction with the β-hydroxycarboxylic acid amides or β-alkoxycarboxylic acid amides used as starting materials in accordance with the invention must be considered surprising, since these starting materials are bifunctional compounds which can enter into reactions both at the β-hydroxy group or β-alkoxy group and at the amide group. Since it is known that hydroxy groups and alkoxy groups are strongly activated by β-positioned carboxyl groups, the expert would expect that the hydroxy or alkoxy group, owing to its particular reactivity, would react preferentially with amines to form β-aminocarboxylic acid amides, that is to say substitution of the hydroxy or alkoxy group by amine. Surprisingly, however, it was found that by observing a temperature range of 100° to 200° C. there is practically no exchange of the hydroxy or alkoxy group in the β-position for amine, but practically only transamidation.

In the process according to the invention, β-substituted carboxylic acid amide and amine are caused to react by simple heating, without the addition of a solvent, wherein the reaction equilibrium is shifted by removing the resulting ammonia to the product side (=N-substituted β-hydroxycarboxylic or β-alkoxycarboxylic acid amide).

The transamidation can be carried out under normal pressure without the addition of a catalyst. The addition of about 5 to 10% of the respective N-substituted β-hydroxycarboxylic or β-alkoxycarboxylic acid amide is advantageous for bridging an initial induction period. To adhere to reaction times of the order of 6 hours, amines having boiling points above about 110° C. are used. The transamidation is usually higher than 95%.

Preferably the amines used are amines that form a homogeneous phase with the melt of the acid amide, or that are partially soluble in the melt of the acid amide or that themselves dissolve a portion of the acid amide.

The particular amine can be used in excess— relative to β-hydroxycarboxylic acid amide—so as to minimize the side reaction of the hydroxyl function with the amide group, which cannot be ruled out when there is a high conversion and which results in polyesters, or, after thermal splitting, in α,β-unsaturated acid.

The β-hydroxycarboxlic acid and β-alkoxycarboxylic acid amides used as starting compounds for the transamidation are produced from β-hydroxycarboxylic and β-alkoxycarboxylic acid nitriles respectively by water addition analogously to DE-PS No. 20 36 126 or A.P. Terentjev et al, J. Obsc. Chim. 26 (1956) 827–830.

Following transamidation, the resulting N-substituted β-hydroxycarboxylic or β-alkoxycarboxylic acid amides are converted catalytically while heating, that is pyrolytically, into the N-substituted α,β-unsaturated carboxylic acid amides and the reaction products formed are isolated from the reaction mixture. If the starting materials used are β-hydroxycarboxylic acid amides, the N-substituted β-hydroxycarboxylic acid amides formed by transamidation are converted by dehydration in the presence of acidic or basic catalysts, optionally with the addition of polymerization inhibitors, into the desired α,β-unsaturated N-substituted carboxylic acid amides. The dehydration can be carried out under reduced pressure. Suitable polymerisation inhibitors are, for example, copper salts or phenol derivatives. Suitable dehydration catalysts include not only acidic catalysts, such as phosphorus pentoxide, phosphoric acid, phosphorus acid or sulphuric acid, but also basic catalysts, such as, for example, sodium hydroxide. Polyphosphoric acid is especially preferred.

The dehydration is carried out at a temperature of about 100° to 250° C., preferably about 150° to 200° C., it takes place in the liquid phase.

If β-alkoxycarboxylic acid amides are used as starting materials, these are converted into the desired α,β-unsaturated N-substituted carboxylic acid amides by splitting off alcohol in the presence of basic catalysts. In this process, the N-substituted β-alkoxycarboxylic acid amide formed first can either be isolated in high yields by distillation before the alcohol is split off or alternatively can be immediately decomposed by pyrolysis.

The alcohol is split off at temperatures of about 70° to 150° C., preferably about 90° to 100° C.

Suitable basic catalysts are, for example, sodium and potassium hydroxide, sodium and potassium carbonate or calcium and barium oxide.

The reaction products are obtained in a high yield and high purity by fractional distillation, optionally in vacuo.

The invention is illustrated by the following examples:

EXAMPLE 1

N-(3-dimethylaminopropyl)acrylamide.

59.3 g of β-hydroxypropionic acid amide and 68 g of 3-dimethylaminopropylamine were heated for 5 hours in a temperature range of 125°–168° C. until the evolution of ammonia was complete. After adding 2 g of polyphosphoric acid the reaction was maintained at 165° C. for 1 hour. Subsequently the reaction was continued in vacuo (water jet vacuum pump) and the resulting reaction products were continuously removed from the reaction mixture by distillation.

Yield: 95 g of N-(3-dimethylaminopropyl)-acrylamide, $Bp_{12}142°$ C.

NMR (CDCl$_3$): δ=1.55–1.95 (m,2); 2.25 (s,6); 2.4 (t,2); 3.1–3.55 (m,2); 5.45–6.3 (m,3).

EXAMPLE 2

N-(3-dimethylaminopropyl)acrylamide.

59.3 g of β-hydroxypropionic acid amide and 68 g of 3-dimethylaminopropylamine were heated for 5 hours in a temperature range of 125°–168° C. until the evolution of ammonia was complete. After adding 1 g of pulverised sodium hydroxide the reaction mixture was distilled.

Yield: 82 g N-(3-dimethylaminopropyl)-acrylamide.

EXAMPLE 3

N-(2-dimethylaminoethyl)acrylamide.

82 g of β-hydroxypropionic acid amide and 92.4 g of dimethylaminoethylamine were heated for 5 hours in a temperature range of 100° to 180° C. until the evolution of ammonia was complete. After adding 3.5 g of polyphosphoric acid the reaction mixture was maintained at 160° C. for one hour. Subsequently the reaction was continued in vacuo (water jet vacuum pump) and the resulting reaction products were continuously removed from the reaction mixture by distillation.

Yield: 123.3 g of N-(2-dimethylaminoethyl)-acrylamide, $Bp_{12}125°$ C.

NMR (CDCl$_3$): δ=2.23 (s,6); 2.45 (t,2); 3.3 (m,2); 5.4–6.25 (m,3); 7.6 (m,1).

EXAMPLE 4

N-(2-diethylaminoethyl)acrylamide.

82 g of β-hydroxypropionic acid amide and 122 g of diethylaminoethylamine were heated for 6 hours in a temperature range of 135°–170° C. until the evolution of ammonia was complete. After adding 7 g of polyphosphoric acid the reaction mixture was maintained at 160° C. for 1 hour. Subsequently the reaction was continued in vacuo (water jet vacuum pump) and the resulting reaction products were continuously removed from the reaction mixture by distillation.

Yield: 134.1 g of N-(2-diethylaminoethyl)-acrylamide $Bp_{12}133°$ C.

NMR (CDCl$_3$): δ=1.05 (t,6); 2.6 (m,6); 3.35 (m,2); 5.4–6.35 (m,3); 7.4 (m,1).

EXAMPLE 5

N-(N',N',2,2-tetramethyl-3-aminopropyl)acrylamide.

89 g of β-hydroxypropionamide and 136.5 g of N,N,2,2-tetramethylpropanediamine-1,3 were heated for 7 hours in a termperature range of 145°–160° C. until the evolution of ammonia was complete. After adding 4.5 g of polyphosphoric acid the reaction mixture was distilled in a water jet vaccum at a sump temperature of approximately 168° C.

Yield: 164 g of N-(N',N',2,2-tetramethyl-3-aminopropyl)acrylamide $Bp_{10}$ 137° C.

NMR ($CDCl_3$): δ=0.9 (s,6); 2.3 (m,8); 3.25 (d,2); 5.4–6.2 (m,3); 8.2 (m,1).

EXAMPLE 6

N-benzylacrylamide.

59 g of β-hydroxypropionamide and 75 g of benzylamine were heated with 50 mg of 2,6-di-t-butyl-p-cresol for 7 hours in a temperature range of 120°–170° C. until the evolution of ammonia was complete. After adding 2.2 g of polyphosphoric acid distillation was carried out in an oil pump vacuum; the subsequent redistillation with the addition of 1 ml of sulphuric acid yielded 92 g of N-benzylacrylamide, $Bp_{0.1}$ 113° C., which crystallized in the receiver. Mp (crude product): 53° C.

NMR ($CDCl_3$): δ=4.35 (d,2); 5.35–6.25 (m,3); 7.2 (s,5).

EXAMPLE 7

N-cyclohexylacrylamide.

59 g of β-hydroxypropionamide and 69.4 g of cyclohexylamine were heated with 50 mg of 2,6-di-t-butyl-pcresol for 5 hours in a temperature range of 130°–170° C. until the evolution of ammonia was complete. After adding 2.5 g of polyphosphoric acid the reaction mixture was maintained at 164° C. for 1 hour and then distilled in a water jet vacuum. The main run was taken off between 140° and 160° C. at 11 bar and crystallized in the receiver.

Yield: 84 g of N-cyclohexylacrylamide: Mp 110° C.

NMR ($CDCl_3$): δ=0.85–2.2 (m,10); 3.8 (m,1); 5.4–6.4 (m,3).

EXAMPLE 8

N-dodecylacrylamide.

82 g of β-hydroxypropionamide and 195 g of dodecylamine were heated with 50 mg of 2,6-di-t-butyl-p-cresol for 4 hours in a temperature range of 130° C. to 190° C. unitl the evolution of ammonia was complete. After adding 5 g of polyphosphoric acid the reaction mixture was maintained at 160° C. for 1 hour and then distilled in an oil pump vacuum. The main run was taken off between 148° C. and 168° C. at 0.3 bar and crystallized in the receiver.

Yield: 187 g of N-dodecylacrylamide; Mp (crude product): 49° C.

NMR ($CDCl_3$): δ=0.6–2.0 (m,23); 3.3 (m,2); 5.4–6.3 (m,3); 7.4 (m,1).

EXAMPLE 9

N-stearylacrylamide.

89 g of β-hydroxypropionamide and 283 of stearylamine were heated with 50 mg of 2,6-di-t-butyl-p-cresol for 6 hours at 160° C. until the evolution of ammonia was complete. After adding 7 g of polyphosphoric acid and 100 mg of copper salicylate, the reaction mixture was distilled in an oil pump vacuum. The main run was taken off at 197° C. (0.025 bar) and solidified in the receiver.

Yield: 233 g of N-stearylacrylamide Softening point: 58°–60° C.

NMR ($CDCl_3$): δ=0.2–2.1 (m,35); 3.1–3.6 (m,2); 5.5–6.3 (m,3).

EXAMPLE 10

N-(3-dimethylaminopropyl)crotonic acid amide.

103.1 g of 3-hydroxybutyric acid amide and 107.3 g of 3-dimethylaminopropylamine were heated for 16 hours in a temperature range of 146°–158° C. After adding 4 g of polyphosphoric acid the reaction mixture was maintained at 160° C. for 1 hour. The reaction was then continued in vacuo (water jet vacuum pump) and the resulting reaction products were continously removed from the reaction mixture by distillation.

Yield: 138 g of N-(3-dimethylaminopropyl)-crotonic acid amide $Bp_{12}$ 158° C.

NMR ($CDCl_3$): δ=1.7 (t,2); 1.83 (dd,3); 2.15–2.6 (m,8); 3.35 (m,2); 5.6–7 (m,2).

EXAMPLE 11

N-(2-dimethylaminoethyl)crotonic acid amide.

103.1 g of hydroxybutyric acid amide and 122 g of 2-diethylaminoethylamine were heated for 13 hours in a temperature range of 150°–160° C. After adding 4 g of polyphosphoric acid the reaction mixture was maintained at 160° C. for 1 hour; the reaction was then continued in vacuo (water jet vacuum pump) and the resulting reaction products were continuously removed from the reaction mixture by distillation.

Yield: 153 g of N-(2-diethylaminoethyl)-crotonic acid amide $Bp_{12}$ 165° C.

NMR ($CDCl_3$): δ=1.05 (t,6); 1.83 (dd,3); 2.35–2.8 (m,6); 3.2–3.5 (m,2); 5.65–7.2 (m,2 olefinic protons+1 amide proton).

EXAMPLE 12

N-(2-dimethylaminoethyl)crotonic acid amide.

103.1 g of 3-hydroxybutyric acid amide and 92.6 g of dimethylaminoethylamine were heated for 15 hours at a temperature range of 122°–160° C. After adding 4 g of polyphosphoric acid, the reaction mixture was maintained at 165° C. for 1 hour and then distilled in a water jet vacuum.

Yield: 130 g of N-(2-dimethylaminoethyl)-crotonic acid amide, $Bp_{12}$ 152°–155° C.

NMR ($CDCl_3$): δ=1.88 (dd,3); 2.15–2.65 (m,8); 3.2–3.6 (m,2); 5.65–7.25 (m,2 olefinic protons+1 amide proton)

The following Examples 13–18 illustrate the production of the N-substituted β-alkoxycarboxylic acid amides obtained as intermediates and Examples 19–26 illustrate the production of the α,β-unsaturated N-substituted carboxylic acid amides.

EXAMPLE 13

N-(3-dimethylaminopropyl)-3-methoxypropionamide.

103.1 g (1.0 mole) of 3-methoxypropionamide are heated with 107.3 g (1.05 mole) of 3-dimethylaminopropylamine for 6 hours in a temperature range of 145°–170° C. until the evolution of ammonia is complete. In the subsequent distillation in a high vacuum 176 g (0.93 mole=93.5% of the theoretical yield) of a colorless liquid are obtained having $Bp_{0.1}$ of 97°–99° C.

NMR ($CCl_4$): δ=1.3–1.8 (m,2); 2.1–2.5 (m,4); 2.15 (s,3); 3.05–3.35 (m,2); 3.35 (s,3); 3.55 (t,2); 7.05 (m,1).

EXAMPLE 14

N-(3-dimethylaminopropyl)-3-ethoxypropionamide.

117.2 g of (1.0 mole) of 3-ethoxypropionamide are heated with 107.3 g (1.05 mole) of 3-dimethylaminopropylamine for 6 hours in a temperature range of 145°–170° C. until the evolution of ammonia is complete. In the subsequent distillation in a high vacuum 184 g (0.91 mole = 91% of the theoretical yield) of colorless liquid are obtained having a $Bp_{0.1}$ of 114°–118° C.

NMR $(CCl_4)$:$\delta$ = 1.15 (t,3); 1.4–1.85 (m,2); 2.0–2.5 (m,4); 2.2 (s,6); 3.0–3.8 (m,6); 7.5 (m,1).

EXAMPLE 15

N-(3-dimethylaminopropyl)-3-isopropoxypropionamide.

131.2 g (1.0 mole) of 3-isopropoxypropionamide are heated with 1.07.3 g (1.05 mole) of 3-dimethylaminopropylamine for 6 hours in a temperature range of 145°–170° C. until the evolution of ammonia is complete. In the subsequent distillation in a high vacuum 198 g (0.92 mole = 91.5% of the theoretical yield) of colorless liquid are obtained having a $Bp_{0.1}$ of 128°–132° C.

NMR $(CCl_4)$: $\delta$ = 1.2 (d,6); 1.35–1.9 (m,2); 2.1–2.55 (m,4); 2.2 (s,6); 2.9–3.8 (m,5); 7.45 (m,1).

EXAMPLE 16

N-(3-dimethylaminopropyl)-3-n-butoxypropionamide.

145.2 g (1.0 mole) of 3-n-butoxypropionamide are heated with 107.3 g (1.05 mole) of 3-dimethylaminopropylamine for 8 hours in a temperature range of 150°–170° C. until the evolution of ammonia is complete. In the subsequent distillation in a high vacuum, 204 g (0.89 mole = 89% of the theoretical yield) of colorless liquid are obtained having a $Bp_{0.1}$ of 122° to 124° C.

NMR $(CDCl_3)$: $\delta$ = 0.75–2.0 (m,9); 2.15–2.6 (m,4); 2.25 (s,6); 3.1–3.8 (m,6); 7.1 (m,1).

EXAMPLE 17

N-(2-dimethylaminoethyl)-3-methoxypropionamide.

103.1 g (1.0 mole) of 3-methoxypropionamide are heated with 92.6 g (1.05 mole) of 2-dimethylaminoethylamine for 6 hours in a temperature range of 125°–170° C. until the evolution of ammonia is complete. In the subsequent distillation in a high vacuum 165 g (0.95 mole = 95% of the theoretical yield) of colorless liquid are obtained having a $Bp_{0.1}$ of 102°–105° C.

NMR $(CCl_4)$:$\delta$ = 2.1–2.7 (m,4); 2.25 (s,6); 3.1–3.45 (m,2); 3.35 (s,3); 3.6 (t,2); 7.1 (m,1).

EXAMPLE 18

N-(3-dimethylaminopropyl)acrylamide.

188.3 g (1.0 mole) of N-(3-dimethylaminopropyl)-3-methoxypropionamide (according to Example 13) are heated with 1.5 g of sodium hydroxide at 90°–110° C. in a high vacuum. Within about 30 minutes methanol is split off, vigorous forming occurring. The temperature is increased and 103 g (0.66 mole = 66% of the theoretical yield) of colorless oil having a $Bp_{0.1}$ of 96°–100° C. are distilled off.

NMR $(CDCl_3)$:$\delta$ = 1.55–1.95 (m,2); 2.25 (s,6); 2.4 (t,2); 3.1–3.55 (m,2); 5.45–6.3 (m,3).

EXAMPLE 19

N-(2-dimethylaminoethyl)acrylamide.

174.2 g (1.0 mole) of N-(2-dimethylaminoethyl)-3-methoxypropionamide (according to Example 17) are heated with 1.5 g of sodium hydroxide in a high vacuum at 90° to 110° C. Within about 30 minutes the methanol is split off, vigorous foaming occurring. The temperature is increased and 85 g (0.6 mole = 60% of the theoretical yield) of colorless oil having a $Bp_{0.1}$ of 85°–90° C. are distilled off.

NMR $(CDCl_3)$:$\delta$ = 2.23 (s,6); 2.45 (t,2); 3.3 (m,2); 5.4–6.25(m,3); 7.6 (m,1).

EXAMPLE 20

N-(2-diethylaminoethyl)acrylamide. 103.1 g (1.0 mole) of 3-methoxypropionamide are heated with 122 g (1.05 mole) of 2-diethylaminoethylamine for 6 hours in a temperature range of 135°–170° C. until the evolution of ammonia is complete. The mixture is allowed to cool, 1.5 g of sodium hydroxide is added, and the mixture is heated in a high vacuum at 90°–110° C. The methanol is split off within about 30 minutes, vigorous foaming occurring. The temperature is increased and 99 g (0.58 mole = 58% of the theoretical yield) of a colorless oil having a $Bp_{0.1}$ of 95°–100° C. are distilled off.

NMR $(CDCl_3)$:$\delta$ = 1.05 (t,6); 2.6 (m,6); 3,35 (m,2) 5.4–6.35 (m,3); 7.4 (m,1).

EXAMPLE 21

N-(N',N',2,2-tetramethyl-3-aminopropyl)acrylamide.

103.1 g (1.0 mole) of 3-methoxypropionamide are heated with 136.7 g (1.05 mole) of N,N,2,2-tetramethylpropanediamine-1,3 for 8 hours in a temperature range of 145°–170° C. until the evolution of ammonia is complete. The mixture is allowed to cool, 1.5 g of sodium hydroxide is added and the mixture is heated in a high vacuum at 90°–110° C. The methanol is split off within about 30 minutes, vigorous foaming occurring. The temperature is increased and 140 g (0.65 mole = 65% of the theoretical yield) of colorless oil having a $Bp_{0.1}$ of 108°–110° C. are distilled off.

NMR $(CDCl_3)$:$\delta$ = 0.9 (s,6), 2.3 (m,8); 3.25(d,2); 5.4–6.2 (m,3); 8.2 (m,1).

EXAMPLE 22

N-cyclohexylacrylamide.

103.1 g (1.0 mole) of 3-methoxypropionamide are heated with 104.1 g (1.05 mole) of cyclohexylamine for 8 hours in a temperature range of 130°–170° C. until the evolution of ammonia is complete. The mixture is allowed to cool, 1.5 g of sodium hydroxide is added and the mixture is heated in a high vacuum at 90°–110° C. The methanol is split off within about 30 minutes, vigorous foaming occurring. The temperature is increased and 93.5 g (0.61 mole = 61% of the theoretical yield) of N-cyclohexylacrylamide having a $Bp_{0.1}$ of 124°–128° C., which solidifies into crystalline form in the receiver, are distilled off.

NMR $(CDCl_3)$:$\delta$ = 0.85–2.2 (m,10); 3.8 (m,1); 5.4–6.4 (m,3).

EXAMPLE 23

N-benzylacrylamide 103.1 g (1.0 mole) of 3-methoxypropionamide are heated with 112.5 g (1.05 mole) of benzylamine for 8 hours in a temperature range of 120°–170° C. until the evolution of ammonia is complete. The mixture is allowed to cool, 1.5 g of sodium hydroxide are added, and the mixture is heated in a high vacuum at 90°–110° C. The methanol is split off within approximately 30 minutes, vigorous foaming occurring. The temperature is increased and 113 g (0.7 mole=70% of the theoretical yield) of N-benzylamide having a $Bp_{0.1}$ of 112°–115° C., which solidifies into crystalline form in the receiver, are distilled off.

NMR $(CDCl_3): \delta = 4.35$ (d,2); 5.35–6.25 (m,3); 7.2 (s,5).

EXAMPLE 24

N-dodecylacrylamide.

103.1 g (1.0 mole) of 3-methoxypropionamide are heated with 194.6 g (1.05 mole) of dodecylamine in a temperature range of 130°–170° C. until the evolution of ammonia is complete. The mixture is allowed to cool, 1.5 g of sodium hydroxide is added and the mixture is heated in a high vacuum at 90° to 110° C. The methanol is split off within about 30 minutes, vigorous foaming occurring. The temperature is increased and 172.4 g (0.72 mole=72% of the theoretical yield) of N-dodecylacrylamide having a $Bp_{0.1}$ of 165°–170° C., which solidifies into crystalline form in the receiver, are distilled off.

NMR $(CDCl_3): \delta 0.6$–2.0 (m,23); 3.3 (m,2); 5.4–6.3 (m,3); 7.4 (m,1).

EXAMPLE 25

N-(3-dimethylaminopropyl)methacrylamide.

117.2 g (1.0 mole) of 2-methyl-3-methoxypropionamide are heated with 107.3 g (1.05 mole) of 3-dimethylaminopropylamine for 20 hours in a temperature range of 145°–175° C. until the evolution of ammonia is complete. The mixture is allowed to cool, 1.5 g of sodium hydroxide is added and the mixture is heated in a high vacuum at 90° to 110° C. The methanol is split off within about 30 minutes, vigorous foaming occurring. The temperature is increased and 122 g (0.72 mole=72% of the theoretical yield) of colorless oil having a $Bp_{0.1}$ of 106°–110° C. are distilled off.

NMR $(CCl_4): \delta = 1.35$–1.85 (m,2); 1.9 (s,3) 2.2 (s,6); 2.35 (t,2); 3.05–3.45 (m,2); 5.1–5.7 (m,2); 7.8 (m,1).

EXAMPLE 26

N-(3-dimethylaminopropyl)crotonic acid amide.

117.2 g (1.0 mole) of 3-methoxybutyric acid amide are heated with 103.7 g (1.05 mole) of 3-dimethylaminopropylamine for 10 hours in a temperature range of 145°–175° C. The mixture is allowed to cool, 1.5 g of sodium hydroxide are added and the mixture is heated in a high vacuum at 120°–130° C. The methanol is split off within about 30 minutes, vigorous foaming occurring. The temperature is increased and 130 g (0.76 mole=76% of the theoretical yield) of light yellow oil having a $Bp_{0.1}$ of 132°–134° C. are distilled off.

NMR $(CDCl_3): \delta = 1.7$ (t,2); 1.83 (dd,3); 2.15–2.6 (m,8); 3.35 (m,2); 5.6–7.0 (m,2); 7.4 (m,1).

It will be appreciated that the instant specification and examples are set forth by way of illustration and not limitation, and that various modifications and changes may be made without departing from the spirit and scope of the present invention.

We claim:

1. A process for the manufacture of an $\alpha,\beta$-unsaturated N-substituted carboxylic acid amide of the formula

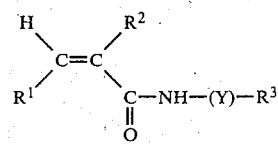

in which
$R^1$ and $R^2$ are independently is H or $CH_3$,
Y is a divalent organic radical having 2–30 carbon atoms,
$R^3$ is H or a radical of the formula $-N(R^4)(R^5)$, and
$R^4$ and $R^5$ each independently is an alkyl radical having 1 to 4 carbon atoms, comprising reacting an $\alpha,\beta$-substituted carboxylic acid amid of the formula

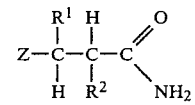

in which
Z is a hydroxy group or an alkoxy radical having 1 to 4 carbon atoms,
with an amine of the formula
$H_2N-(Y)-R_3$ at a temperature of about 100° to 200° C. with the elimination of ammonia thereby to form an N-substituted $\beta$-hydroxycarboxylic or $\beta$-alkoxycarboxylic acid amide of the formula

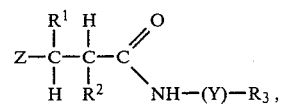

and heating such amide in the presence of a catalyst thereby to produce the corresponding $\alpha,\beta$-unsaturated carboxylic acid amide.

2. A process according to claim 1, in which Z is a hydroxy group and heating of the N-substituted $\beta$-hydroxycarboxylic acid amide to produce the N-substituted $\alpha,\beta$-unsaturated carboxylic acid amide is effected in the presence of an acidic or basic catalyst.

3. A process according to claim 2, in which phosphorus pentoxide, phosphoric acid, phosphorous acid, polyphosphoric acid, sulphuric acid or sodium hydroxide is used as the catalyst.

4. A process according to claim 2, in which heating is effected at a temperature of about 100° to 250° C.

5. A processing according to claim 3, in which Y is a radical of the formula $-(Y_1)_m-(Y_2)_n-(Y_3)_t$, in which $Y_1$, $Y_2$ and $Y_3$ each independently is an alkylene radical or the radical of a cyclic organic ring system having 5 or 6 carbon atoms, and the sum of m, n and t is 2 or 3, and heating is effected in the liquid phase at a temperature of about 150° to 200° C., the resulting $\alpha,\beta$-unsaturated N-substituted carboxylic acid amide being isolated from the reaction mixture by distillation under reduced pressure.

6. A process according to claim 1, in which Z is an alkoxy radical and heating of the N-substituted α,β-alkoxycarboxylic acid amide to produce the N-substituted α,β-unsaturated carboxylic acid amide by splitting off alcohol is effected in the presence of a basic catalyst.

7. A process according to claim 6, in which sodium hydroxide, potassium hydroxide, sodium carbonate, potassium carbonate, calcium oxide and/or barium oxide is used as the basic catalyst for splitting off the alcohol.

8. A process according to claim 7, in which the alcohol is split off at a temperature of about 70°–150° C.

9. A process according to claim 7, in which Y is a radical of the formula—$(Y_1)_m$—$(Y_2)_n$—$(Y_3)_t$, in which $Y_1$, $Y_2$ and $Y_3$ each independently is an alkylene radical or the radical of a cyclic organic ring system having 5 or 6 carbon atoms, and the sum of m, n and t is 2 or 3, and the alcohol is split off in the liquid phase at a temperature of about 90° to 110° C., the resulting α,β-unsaturated N-substituted carboxylic acid amide being isolated from the reaction mixture by distillation under reduced pressure.

10. A process according to claim 1, in which the heating of the α,β-hydroxycarboxylic acid amide or α,β-alkoxycarboxylic acid amide to produce the N-substituted α,β-unsaturated carboxylic acid amide is effected in the liquid phase.

11. A process according to claim 1, including the further step of isolating the resulting α,β-unsaturated N-substituted carboxylic acid amide from the reaction mixture by distillation under reduced pressure.

* * * * *